United States Patent
Kitajima et al.

(10) Patent No.: US 7,485,665 B2
(45) Date of Patent: Feb. 3, 2009

(54) MEDICINAL COMPOSITION

(75) Inventors: Akihiko Kitajima, Kyoto (JP); Osamu Kamoda, Kyoto (JP); Akihiro Ohsako, Kyoto (JP); Toshiharu Yanagi, Osaka (JP)

(73) Assignee: Nagase Chemtex Corporation, Osaka (JP)

( * ) Notice: Subject to any disclaimer, the term of this patent is extended or adjusted under 35 U.S.C. 154(b) by 0 days.

(21) Appl. No.: 10/526,780

(22) PCT Filed: Sep. 12, 2002

(86) PCT No.: PCT/JP02/09390

§ 371 (c)(1),
(2), (4) Date: May 20, 2005

(87) PCT Pub. No.: WO2004/024143

PCT Pub. Date: Mar. 25, 2004

(65) Prior Publication Data

US 2005/0239861 A1    Oct. 27, 2005

(51) Int. Cl.
*A61K 31/40* (2006.01)
*C07D 207/04* (2006.01)

(52) U.S. Cl. ........................... 514/426; 548/557

(58) Field of Classification Search ................ 514/426; 548/557

See application file for complete search history.

(56) References Cited

U.S. PATENT DOCUMENTS 5,143,935 A    9/1992   Fujiwara et al. ............. 514/426

FOREIGN PATENT DOCUMENTS

JP           5-17434       1/1993

*Primary Examiner*—Ardin Marschel
*Assistant Examiner*—Amy A Lewis
(74) *Attorney, Agent, or Firm*—Wenderoth, Lind & Ponack, L.L.P.

(57) ABSTRACT

The present invention relates to an ameliorant for improving the movement of the digestive tract comprising, as an active ingredient, 4-amino-5-chloro-2-methoxy-N-[(2S,4S)-2-hydroxymethyl-4-pyrrolidinyl]benzamide or an acid addition salt thereof which is a metabolite of 4-amino-5-chloro-2-methoxy-N-[(2S,4S)-1-ethyl-2-hydroxymethyl-4-pyrrolidinyl]benzamide or an acid addition salt thereof, having high biding affinity for a serotonin receptor 4 ($5HT_4$) and causing no arteritis and thrombus formation; a medicinal composition for improving the movement of the digestive tract comprising the said ameliorant and a pharmaceutically acceptable carrier; and a treating method for promoting the movement of the digestive tract, which comprises using the said medicinal composition for improving the movement of the digestive tract.

2 Claims, 3 Drawing Sheets

MEDICINAL COMPOSITION

This application is a U.S. national stage of International Application No. PCT/JP02/09390 filed Sep.12, 2002.

TECHNICAL FIELD

The present invention relates to an ameliorant for improving the movement of the digestive tract of a human and an animal containing as an active ingredient a compound which is suitable for activating the movement of the digestive tract, inter alia, stomach to rapidly eliminate abnormal retention of an ingested food in the organ, has a peripheral acting site, and has no side effect such as arteritis, that is, 4-amino-5-chloro-2-methoxy-N-[(2S,4S)-2-hydroxymethyl-4-pyrrolidinyl]benzamide or an acid addition salt thereof, a medicinal composition comprising the active ingredient and a pharmaceutically acceptable carrier, a method for improving disorder of the movement dysfunction of the digestive tract comprising administering a composition containing an effective amount of the active compound to a patient, and use of the compound for preparing the composition.

BACKGROUND TECHNIQUE

A compound having a generic name of metoclopramide is widely known as a compound having nature of promoting the movement of stomach, but induces extrapyramidal disorder and other undesirable disorders due to action on central nervous system. In addition, a compound having a generic name of cisapride has been put into practice as a digestive tract movement activator, but use thereof has been stopped due to inducement of ventricular arrhythmia.

4-Amino-5-chloro-2-methoxy-N-[(2S,4S)-1-ethyl-2-hydroxymethyl-4-pyrrolidinyl]benzamide (also referred to as TKS159 in some cases) or an acid addition salt thereof which is said to have no or extremely weak action on central nervous system is known as a compound having action of promoting the movement of the digestive tract, inter alia, stomach (JP-A-17434/1993). However, the present applicant progressed development of TKS159 which is a representative compound of the invention of the above patent and, when TKS159 was orally administered repeatedly in a safety test using an experimental animal, inter alia, a beagle dog, findings of disorders such as thrombus formation, arteritis, encephalomalacia and the like were observed. After all, occurrence of such disorders truly shows that TKS159 is not suitable for use as a medicine. The present inventors thought that various disorders which had not appeared in a mouse or a rat are findings of disorders caused by 4-amino-5-chloro-2-methoxy-N-[(2S,4S)-2-hydroxymethyl-4-pyrrolidinyl]benzamide or an acid addition salt thereof found to be a metabolite of the compound specifically produced in a beagle dog and they have repeatedly administered 4-amino-5-chloro-2-methoxy-N-[(2S, 4S)-2-hydroxymethyl-4-pyrrolidinyl]benzamide or an acid addition salt thereof to a beagle dog. Unexpectedly, it was found out that findings of various disorders seen upon administration of TKS159 were not observed. Moreover, it was found out that 4-amino-5-chloro-2-methoxy-N-[(2S,4S)-2-hydroxymethyl-4-pyrrolidinyl]benzamide or an acid addition salt thereof is a compound having the ability of improving the movement of the digestive tract equivalent to or superior over that of TKS159 or an acid addition salt thereof. That is, it was found out that 4-amino-5-chloro-2-methoxy-N-[(2S,4S)-2-hydroxymethyl-4-pyrrolidinyl]benzamide or an acid addition salt thereof which can avoid occurrence of disorders such as thrombus formation, arteritis, encephalomalacia and the like can be effectively used as an ameliorant for improving the movement of the digestive tract containing this compound as an active ingredient. Needless to say, it is natural that desired attribute of a drug used in treatment is sufficient possession of required action, and it is widely sought to provide a drug from which occurrence of not preferable action which is reportedly impossible to avoid due to inevitable attendance to the drug, has been removed. In diseases other than diseases directly influencing on a life, such the tendency is further intense. It is widely known that there are many cases where although a drug has sufficient required action, since occurrence of a few unavoidable not preferable actions can not be avoided, it could not actually play a role as a therapeutic drug. In addition, although the aforementioned patent describes 4-amino-5-chloro-2-methoxy-N-(5-hydroxymethylpyrrolidin-3-yl)benzamide, but 4-amino-5-chloro-2-methoxy-N-[(2S,4S)-2-hydroxymethyl-4-pyrrolidinyl]benzamide is a novel compound as stereo isomer or optical isomer.

DISCLOSURE OF THE INVENTION

The present invention has been made based on the aforementioned findings, and relates to an ameliorant for improving the movement of the digestive tract, which avoids side effect such as arteritis, containing 4-amino-5-chloro-2-methoxy-N-[(2S, 4S)-2-hydroxymethyl-4-pyrrolidinyl]benzamide or an acid addition salt thereof as an active ingredient. Further, the present invention relates to a novel medicinal composition for administering to a human or a mammal (e.g. dog, cat, cow, horse, sheep etc.), comprising the 4-amino-5-chloro-2-methoxy-N-[(2S,4S)-2-hydroxymethyl-4-pyrrolidinyl]benzamide or an acid addition salt thereof, and a pharmaceutically acceptable carrier.

The ameliorant for improving the movement of the digestive tract of the present invention and a novel medicinal composition containing the same relate to a novel medicinal composition comprising a compound which can avoid side effect concomitantly caused in 4-amino-5-chloro-2-methoxy-N-[(2S,4S)-1-ethyl-2-hydroxymethyl-4-pyrrolidinyl]benzamide or an acid addition salt thereof such as thrombus formation, arteritis and the like, that is, 4-amino-5-chloro-2-methoxy-N-[(2S,4S)-2-hydroxymethyl-4-pyrrolidinyl]benzamide (referred to as TM161 in some cases) or an acid addition salt thereof, and a pharmaceutically acceptable carrier.

The compound TM161 or an acid addition salt thereof was found out as a metabolite of a 4-amino-5-chloro-2-methoxy-N-[(2S,4S)-1-ethyl-2-hydroxymethyl-4-pyrrolidinyl]benzamide compound or an acid addition salt thereof when administered to a living body, inter alia, a beagle dog and, surprisingly it was made clear in study of the present inventors that the compound or the salt has characteristic capable of avoiding occurrence of side effect such as thrombus formation, arteritis and the like which were concomitantly caused inevitably in administration of 4-amino-5-chloro-2-methoxy-N-[(2S,4S)-1-ethyl-2-hydroxymethyl-4-pyrrolidinyl]benzamide. In addition, it was also made clear that the compound or the salt is superior over TKS159 or an acid addition salt thereof in the ability to improve the movement of the digestive tract. Further, it was also made clear that 4-amino-5-chloro-2-methoxy-N-[(2S,4S)-2-hydroxymethyl-4-pyrrolidinyl]benzamide or an acid addition salt thereof acts as an agonist such that binding with a serotonin 4 ($5HT_4$) receptor is preferential to binding to other receptor, for example, a dopamine $D_2$ receptor.

Thereby, it has also been elucidated that the compound is a compound which can reduce side effect such as sedative action, extrapyramidal disorder, exacerbation of prolactin secretion and the like which is said to be caused by binding with dopamine $D_2$.

The present invention has been made based on such the various new findings and, according to the present invention, there are provided an ameliorant for improving the movement of the digestive tract containing as an active ingredient 4-amino-5-chloro-2-methoxy-N-[(2S,4S)-2-hydroxymethyl-4-pyrrolidinyl]benzamide or an acid addition salt thereof, which has high binding affinity for a serotonin receptor 4 ($5HT_4$), and can avoid occurrence of side effect such as thrombus formation, arteritis and the like inevitably caused concomitantly in administration of 4-amino-5-chloro-2-methoxy-N-[(2S,4S)-1-ethyl-2-hydroxymethyl-4-pyrrolidinyl]benzamide or an acid addition salt thereof, and a medicinal composition containing the same as an active ingredient, and a pharmaceutically acceptable carrier. Since it is an indispensable attribute for a medicinal composition that side effect is avoided as much as possible, the present invention is meaningful.

A true medical invention is first constituted after not only useful pharmacological activity but also no serious side effect is confirmed. That is, the present invention relates to an ameliorant for improving the movement of the digestive tract which has been confirmed to bean effective and safe medicine not accompanied with occurrence of side effect.

The present invention relates to:

(1) an ameliorant for improving the movement of the digestive tract comprising as an active ingredient 4-amino-5-chloro-2-methoxy-N-[(2S,4S)-2-hydroxymethyl-4-pyrrolidinyl]benzamide or an acid addition salt thereof, which has high binding affinity for a serotonin receptor 4($5HT_4$), and does not cause arteritis and thrombus formation, (2) a medicinal composition for improving the movement of the digestive tract, comprising as an active ingredient 4-amino-5-chloro-2-methoxy-N-[(2S,4S)-2-hydroxymethyl-4-pyrrolidinyl]benzamide or an acid addition salt thereof, which has high binding affinity for a serotonin receptor 4 ($5HT_4$), and does not cause arteritis and thrombus formation, and a pharmaceutically acceptable carrier, (3) a treating method for promoting the movement of the digestive tract, which comprises using an ameliorant for improving the movement of the digestive tract comprising as an active ingredient 4-amino-5-chloro-2-methoxy-N-[(2S, 4S)-2-hydroxymethyl-4-pyrrolidinyl]benzamide or an acid addition salt thereof, which is has high binding affinity for a serotonin receptor 4 ($5HT_4$), and does not cause arteritis and thrombus formation, or using a medicinal composition for improving the movement of the digestive tract comprising the ameliorant and a pharmaceutically acceptable carrier, (4) a method for improving the movement of the digestive tract of a human or an animal, while avoiding occurrence of arteritis, thrombus formation or encephalomalacia, which comprises administering 4-amino-5-chloro-2-methoxy-N-[(2S, 4S)-2-hydroxymethyl-4-pyrrolidinyl]benzamide or an acid addition salt thereof, or a medicinal composition comprising the ameliorant and a pharmaceutically acceptable carrier to a human or a mammal, (5) 4-amino-5-chloro-2-methoxy-N-[(2S,4S)-2-hydroxymethyl- 4-pyrrolidynyl]benzamide or an acid addition salt thereof, -(6) 4-amino-5-chloro-2-methoxy-N-[(2S,4S) -2-hydroxymethyl-4Pyrrolidinyl] benzamide in which an amino group at position 4 or/and an amino group of the pyrrolidinyl group may be protected, or an acid addition salt thereof, (7) a process for preparing 4-amino-5-chloro-2-methoxy-N- [(2S, 4S) -2-hydroxymethyl-4-pyrrolidinyl] benzamide or an acid addition salt thereof, which comprises reacting 4-amino-5-chloro-2-methoxybenzoic acid having an optionally protected amino group or a reactive derivative thereof with (2S, 4S) -4-amino-N-acyl-2-hydroxymethylpyrrolidine to obtain 4-amino- 5-chloro- 2-methoxy-N-[(2S,4S)-1-acyl-2- hydroxymethyl-4-pyrrolidinyl]benzamide or an acid addition salt thereof, and eliminating a protecting group and the acyl group, when a protecting group is used in the acyl group, (8) (2S,4S)4-amino-N-acyl-2-hydroxymethylpyrrolidine having an optionally protected amino group, (9) the compound according to the above (8), wherein a protecting group for an amino group is an acyl group, and the acyl group and an acyl group of N-acyl are selected from formyl, acetyl, propionyl and benzoyl, and (10) the compound according to the above (8), wherein the acyl group is acetyl. The present invention will be explained in more detail below by describing embodiments, but they should not be construed as limiting the scope of this invention.

BEST MODE FOR CARRYING OUT THE INVENTION

Figure 1:
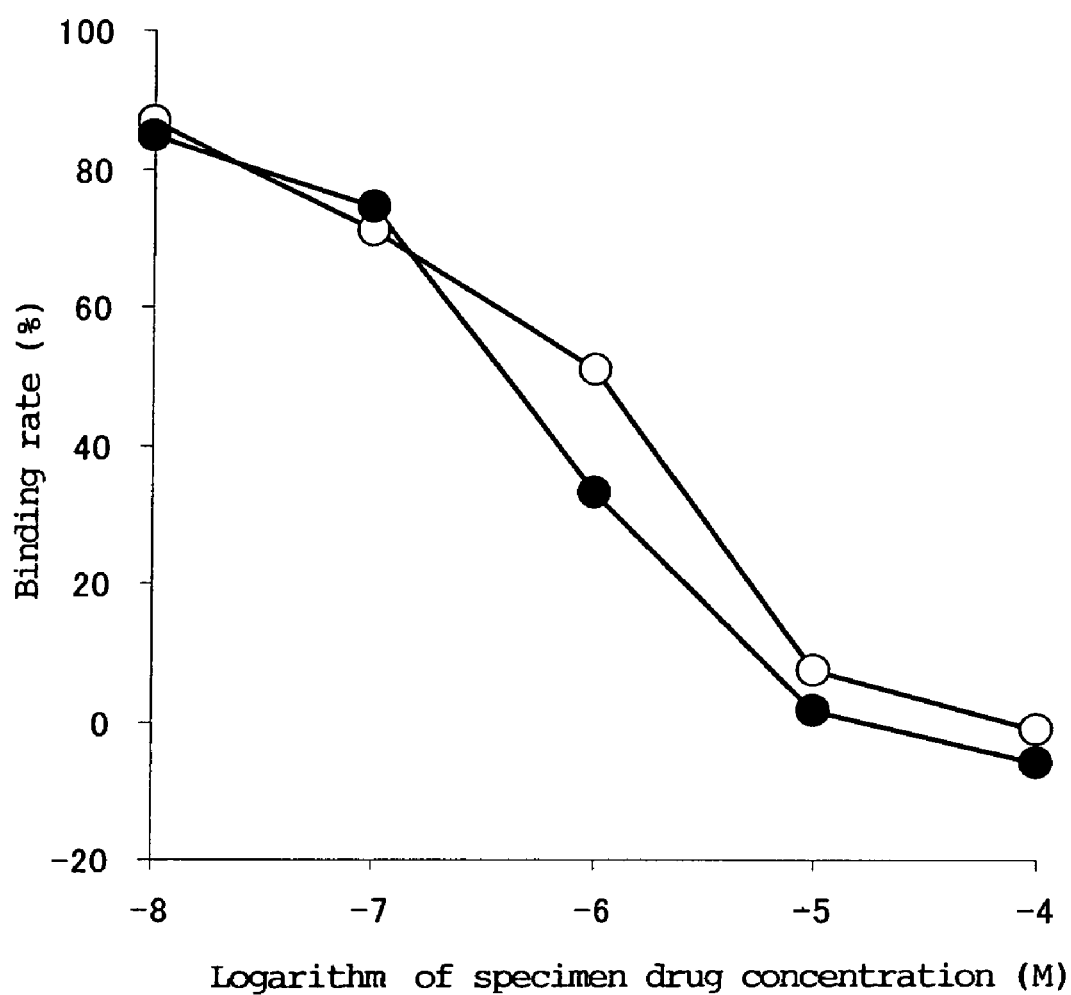
FIG. 1 shows a change in binding affinity for a serotonin receptor 4, of a specimen drug. An abscissa axis indicates a concentration (molar concentration; logarithmic expression) of a specimen drug, and an ordinate axis indicates a ratio of binding of a serotonin receptor 4 and [$^3$H]GR113808. ●---● indicates a specimen compound obtained in Example 9, and ○---○ indicates TK5159 hydrochloride. As a concentration of a specimen drug grows higher, an amount of [$^3$H] GR113808 bound to a serotonin receptor 4 is reduced. That is, it is indicated that a specimen drug binds to a serotonin receptor 4, antagonizing [$^3$H]GR113808 binding to the serotonin receptor 4. It is seen that affinity of a specimen drug obtained in Example 9 for a serotonin receptor 4 is stronger as compared with affinity of TK5159 hydrochloride.

4-Amino-5-chloro-2-methoxy-N-[(2S,4S)-2-hydroxymethyl-4-pyrrolidinyl]benzamide of the present invention or an acid addition salt thereof can be prepared by reacting 4-amino-5- chloro-2-methoxybenzoic acid having an optionally protected amino group represented by the formula (I):

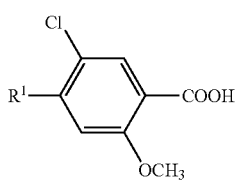

(wherein R¹ represents an optionally protected amino group) or a reactive derivative thereof, with (2S,4S)-4-amino-2-hydroxymethylpyrrolidine having an optionally protected imino group represented by the formula (II):

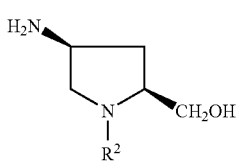

(wherein R² represents a hydrogen atom or a protecting group for an imino group) to prepare a compound represented by the formula (III):

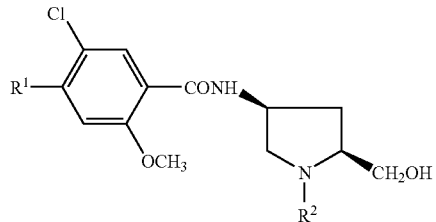

(wherein R¹ and R² are each the same as defined above), and optionally removing a protecting group for an amino group or/and a protecting group for an imino group.

As described above, a compound represented by the formula (III) in which at least one of an amino group or/and an imino group is protected with a protecting group is important as an intermediate for synthesizing 4-amino-5-chloro-2-methoxy-N-[(2S,4S)-2-hydroxymethyl-4-pyrrolidinyl]benzamide (TM161) which is a novel compound, or an acid addition salt thereof. Also, when a protecting group for an amino group or/and a protecting group for an imino group is, like TM161, removed in a living body after administration of a compound (III) to a living body, a compound of the formula (III) can be used like TM161, since it exerts effect of improving the movement of the digestive tract more excellent than that of TKS159 while avoiding side effect such as thrombus formation, arteritis and encephalomalacia. Examples of a protecting group for an amino group and a protecting group for an imino group include an acyl group (e.g. acetyl group), a BOC group, and a benzyloxycarbonyl group. A protecting group which protects an amino group or/and an imino group and can be eliminated in a living body has previously established sufficiently, and such protecting group which can be eliminated in a living body may be adopted as a protecting group also in the present invention. Specifically, as a protecting group which can be eliminated in a living body, an acyl group (e.g. lower alkylcarbonyl group such as acetyl and propionyl), and an alkyloxycarbonyl group (e.g. lower alkyloxycarbonyl group such as methyloxycarbonyl and ethyloxycarbonyl) are preferable.

4-Amino-5-chloro-2-methoxy-N-[(2S,4S)-2-hydroxymethyl-4-pyrrolidinyl]benzamide of the present invention or an acid addition salt thereof, which has high binding affinity for a serotonin receptor 4 ($5HT_4$) and does not cause arteritis, thrombus formation and the like is a metabolite of 4-amino-5-chloro-2-methoxy-N-[(2S,4S)-1-ethyl-2-hydroxymethyl-4-pyrrolidinyl]benzamide or an acid addition salt thereof, and can be prepared more preferably as follows: that is, it can be prepared by subjecting 4-amino-5-chloro-2-methoxybenzoic acid or a derivative in which an amino group thereof is protected, or a reactive derivative thereof (e.g. acid halide, active ester, acid anhydride etc.) and (2S,4S)-4-amino-N-acyl-2-hydroxymethylpyrrolidine to a condensation reaction in a suitable medium optionally in the presence of a condensing agent. Examples of the acyl group include formyl, acetyl, propionyl and benzoyl, and acetyl is preferable. A protecting group for an amino group may be the aforementioned acyl group.

The resulting compound is obtained as an acid addition salt in some cases depending on a condensation method, but when a basic compound is converted into an acid addition salt, it may be converted into an acid addition salt by dissolving it in a suitable solvent and adding a desired acid thereto. Herein, as a suitable medium used in a condensation reaction, a medium which is inert to the starting material or a condensing agent such as tetrahydrofuran, dioxane, benzene, toluene, petroleum hydrocarbon (hexane, heptane, octane, petroleum benzine etc.), dimethylformamide, pyridine, triethylamine, acetonitrile, and chloroform are preferably used. When 4-amino-5-chloro-2-methoxybenzoic acid is converted into a reactive derivative, it includes an acid halide derivative such as acid chloride or acid bromide derived from thionyl chloride or phosphorus tribromide, an acid anhydride such as mixed acid anhydride with ethyl chlorocarbonate, and an active ester derived from ethyl alcohol or p-nitrophenol, and further, an acid imidazolide and an acid pyrrolide obtained by reaction with N, N-dicarbonyldiimidazole or N,N-carbonyldipyrrole. When these reactive derivatives are subjected to a reaction, it is better to use a base such as pyridine, picoline, N-ethylmorpholine, triethylamine and potassium carbonate. Certain cases where a condensing agent is optionally used refers to the case where 4-amino-5-chloro-2-methoxybenzoic acid is subjected to a reaction without being converted into a reactive derivative and, in such cases, a condensing agent is used. Examples of the condensing agent used include N,N-dicyclohexylcarbodiimide, 1,1-sulfinyldiimidazole, 1,1-carbonyldiimidazole, titanium tetrachloride, phosphorus trichloride, phosphorus oxychloride, diethyl chlorophosphite, and o-phenylene chlorophosphite.

A condensation reaction can be preferably performed at room temperature or under warming while stirring. The thus obtained 4-amino-5-chloro-2-methoxy-N-[(2S,4S)-1-acyl-2-hydroxymethyl-4-pyrrolidinyl]benzamide is produced as an acid addition salt in some cases and, when produced as a base form, it is converted into a suitable acid addition salt. Examples of the acid for converting into such acid addition salt include hydrogen chloride, hydrogen bromide, sulfuric acid, hydrogen iodide, carbonic acid, phosphoric acid, formic acid, acetic acid, propionic acid, glycolic acid, glucuronic acid, maleic acid, glutamic acid, methanesulfonic acid, ethanesulfonic acid, toluenesulfonic acid, benzenesulfonic acid, benzoic acid, salicylic acid, phenylacetic acid, mandelic acid, lactic acid, succinic acid, tartaric acid, fumaric acid, and citric acid. For converting into an acid addition salt, a desired acid addition salt can be obtained by mixing and stirring 4-amino-5-chloro-2-methoxy-N-[(2S,4S)-1-acyl-2-hydroxymethyl-4-pyrrolidinyl]benzamide produced as a base with a desired acid among the aforementioned acids in a suitable solvent. An acid addition salt is usually a pharmaceutically acceptable salt.

4-Amino-5-chloro-2-methoxy-N-[(2S,4S)-1-acyl-2-hydroxy methyl-4-pyrrolidinyl]benzamide or an acid addition salt thereof obtained herein is converted into 4-amino-5-chloro-2-methoxy-N-[(2S,4S)-2-hydroxymethyl-4-pyrrolidinyl]benzamide or acid addition salt thereof which can avoid side effect such as arteritis, thrombus formation, and encephalomalacia inevitably occurred in TKS159 or an acid addition salt thereof, via elimination of an acyl group. Herein, elimination of such acyl group is accomplished by addition of sodium hydroxide or potassium hydroxide in an alcohol (methyl alcohol, ethyl alcohol, propyl alcohol etc.), and heating them at reflux.

Thus, an ameliorant for improving the movement of the digestive tract which has high binding affinity for a serotonin receptor 4 ($5HT_4$) and can avoid side effect occurred concomitantly in TKS159 or an acid addition salt thereof such as arteritis and thrombus formation, that is, 4-amino-5-chloro-2-methoxy-N-[(2S,4S)-2-hydroxymethyl-4-pyrrolidinyl] benzamide or an acid addition salt which is a metabolite of 4-amino-5-chloro-2-methoxy-N-[(2S,4S)-1-ethyl-2-hydroxymethyl-4-pyrrolidinyl]benzamide or an acid addition salt can be obtained.

(2S,4S)-4-amino-2-hydroxymethylpyrrolidine having a protected amino acid used in the aforementioned process can be prepared by the following method. (2S,4S)-4-amino-2-hydroxymethylpyrrolidine having a protected imino group can be advantageously prepared in industrial scale by introducing a protecting group into an imino group of 4-hydroxy-L-proline alkyl ester to prepare an N-protected-4-hydroxy-L-proline alkyl ester, converting the hydroxyl group of the thus prepared N-protected-4-hydroxy-L-proline alkyl ester into a mesyloxy group to prepare an N-protected-4-mesyloxy-L-proline alkyl ester, converting the mesyloxy group of the thus prepared N-protected-4-mesyloxy-L-proline alkyl ester into an azido group to prepare an N-protected-4-azido-L-proline alkyl ester, subjecting the thus prepared N-protected-4-azido-L-proline alkyl ester to a reducing reaction to prepare an N-protected-(2S,4S)-4-azido-2-hydroxymethylpyrrolidine, and further subjecting the thus prepared N-protected-(2S,4S)-4-azido-2-hydroxymethylpyrrolidine to a reducing reaction.

As a protecting group in this process, the aforementioned protecting group for an imino group is used, and an acetyl group is preferable. As an alkyl group, a lower alkyl group having a carbon number of 1 to 4 is preferable, and examples thereof include a methyl group and an ethyl group. In addition, it is preferable that the first reduction reaction is performed using sodium borohydride as a reducing agent, and it is preferable to perform the second reduction reaction by catalytic reduction.

4-Amino-5-chloro-2-methoxy-N-[(2S,4S)-2-hydroxymethyl-4-pyrrolidinyl]benzamide or an acid addition salt thereof obtained herein, which is an ameliorant for improving the movement of the digestive tract having high binding affinity for a serotonin receptor 4($5HT_4$) and being capable of avoiding side effect that concomitantly occurs in association with TKS159 or an acid addition salt thereof, such as arteritis and thrombus formation, is formulated into a preparation together with a pharmaceutically acceptable suitable carrier, and is put into practice as a medicinal composition for improving the movement of the digestive tract.

Herein, examples of the pharmaceutically acceptable suitable carrier include excipients (e.g. lactose, glucose, potato starch, corn starch, carboxymethylcellulose, crystalline cellulose, and light silicic anhydride), disintegrators (e.g. starch, calcium carboxymethylcellulose), lubricants (e.g. magnesium stearate, purified talc, calcium stearate), binders (e.g. starch paste solution, hydroxypropylcellulose solution, carboxymethylcellulose solution, gum arabic solution, gelatin solution, hydroxypropylmethylcellulose solution), coloring agents and corrigents. These are selected in conformity with a desired dosage form, prescribed, and formulated into a preparation.

As the preparation of a formulated medicinal composition of the present invention for improving the movement of the digestive tract comprising 4-amino-5-chloro-2-methoxy-N-[(2S,4S)-2-hydroxymethyl-4-pyrrolidinyl]benzamide or an acid addition salt thereof which is an ameliorant for improving the movement of the digestive tract, having high binding affinity for a serotonin receptor 4 ($5HT_4$) and being capable of avoiding side effect that concomitantly occurs in association with TKS159 or an acid addition salt thereof such as arteritis and thrombus formation and a suitable carrier, there are exemplified tablets, capsules, fine granules, granules, injectables, syrups, and dry syrups. A carrier suitable in each of those preparations is used by selecting from the aforementioned carriers. For example, when a preparation which is a formulated medicinal composition for improving the movement of the digestive tract is a tablet, a prescribed amount of 4-amino-5-chloro-2-methoxy-N-[(2S,4S)-2-hydroxymethyl-4-pyrrolidinyl]benzamide or an acid addition salt thereof, which is an ameliorant for improving the movement of the digestive tract, having high binding affinity for a serotonin receptor 4 ($5HT_4$) and being capable of avoiding side effect that concomitantly occurs in association with TKS159 or an acid addition salt thereof such as arteritis and thrombus formation, is placed into a fluidized bed granulator together with a prescribed amount of lactose and crystalline cellulose, and then granulation is performed while an aqueous binder solution is sprayed. Then, a disintegrating agent and a lubricant are added, followed by mixing. A granulated material obtained herein is compressed to a tablet having a prescribed size and weight with a tableting machine.

A content of 4-amino-5-chloro-2-methoxy-N-[(2S,4S)-2-hydroxymethyl-4-pyrrolidinyl]benzamide or an acid addition salt thereof which is an ameliorant for improving of the movement of the tract having high binding affinity for a serotonin receptor 4 ($5HT_4$) and being capable of avoiding side effect that concomitantly occurs in association with TKS159 or an acid addition salt thereof such as arteritis and thrombus formation, as an active ingredient contained in a preparation, is associated with a total dose of an active ingredient per day, and is 0.05 to 10 mg/single dose. Administration frequency is increased or decreased by determination of a physician depending on symptom, administration period, and sensitivity of an individual to an active ingredient, and administration once to three times per day is general.

4-Amino-5-chloro-2-methoxy-N-[(2S,4S)-2-hydroxymethyl-4-pyrrollidinyl]benzamide or an acid addition salt thereof which is an ameliorant for improving the movement of the digestive tract having high binding affinity for a serotonin receptor 4 ($5HT_4$) and being capable of avoiding side effect that concomitantly occurs in association with TKS159 or an acid addition salt thereof, such as arteritis and thrombus formation, as an active ingredient in the present invention, has weaker acute toxicity than that of TKS159 or an acid addition salt thereof in oral administration in an acute toxicity test, and is therefore suitable in oral administration. There are provided an ameliorant for improving the movement of the digestive tract comprising, as an active ingredient, 4-amino-5-chloro-2-methoxy-N-[(2S,4S)-2-hydroxymethyl-4-pirrolidinyl]benzamide or an acid addition salt thereof which is a metabolite of 4-amino-5-chloro-2-methoxy-N-[(2S,4S)-1-ethyl-2-hydroxymethyl-4-pyrrolidinyl]benzamide or an acid addition salt thereof, having high biding affinity for a serotonin receptor 4 ($5HT_4$) and causing no arteritis and thrombus formation, and a medicinal composition for improving the movement of the digestive tract comprising the same and a carrier.

EXAMPLES

Example 1

Measurement of Action of 4-amino-5-chloro-2-methoxy-N-[(2S,4S)-2-hydroxymethyl-4- Pyrrolidinyl] benzaxnide monohydrochioride on serotonin receptor 4

Corpus striatum extracted from a Hartley male guinea pig was homogenized in a 50 mM HEPES-NaOH buffer (pH 7.4), and centrifugation and suspension were repeated to prepare a serotonin receptor 4 sample. The receptor sample was reacted with a solution containing a 0.1 nM radioactive ligand of [$^3$H]-GR113808 and the specimen drug obtained in Example 9 at a prescribed concentration. Then, the solution was filtered by suction using a multifilter MF-12G (glass filter (provided with Whatman GFIC)), and radioactivity of the filter was measured using a scintillation counter (LS6500 Beckman), so that affinity of the specimen drug for a serotonin receptor 4 was measured. Separately, the same procedure was also performed regarding TKS159 hydrochloride, and the affinity was compared.

The results are shown in FIG. 1. $IC_{50}$ is 0.25 µM, which is a lower concentration than 0.45 µM of TKS159 hydrochloride.

Example 2

Measurement of action of 4-amino-5-chloro-2-methoxy-N-[(2S,4S) -2-hydroxymethyl-4-pyrrolidinyl] benzamide monohydrochloride on dopamine $D_2$ receptor Corpus striatum extracted from a Wistar male rat was homogenized in a 50 mM Tris-HCl buffer (pH 7.7), and centrifugation and suspension were repeated to prepare a dopamine D2 receptor sample. The receptor sample was reacted with a solution containing a 0.25 nM radioactive ligand of [$^3$H]-spiperone and the specimen drug obtained in Example 9 at a prescribed concentration. Then, the solution was filtered by suction using a multifilter MF-12G (glass filter (provided with Whatman GF/C)), and radioactivity of the filter was measured using a scintillation counter (LS6500 Beckman), so that affinity of the specimen drug for a dopamine $D_2$ receptor was measured. Separately, the same procedure was also performed regarding TKS159 hydrochloride, and the affinity was compared.

Figure 2:
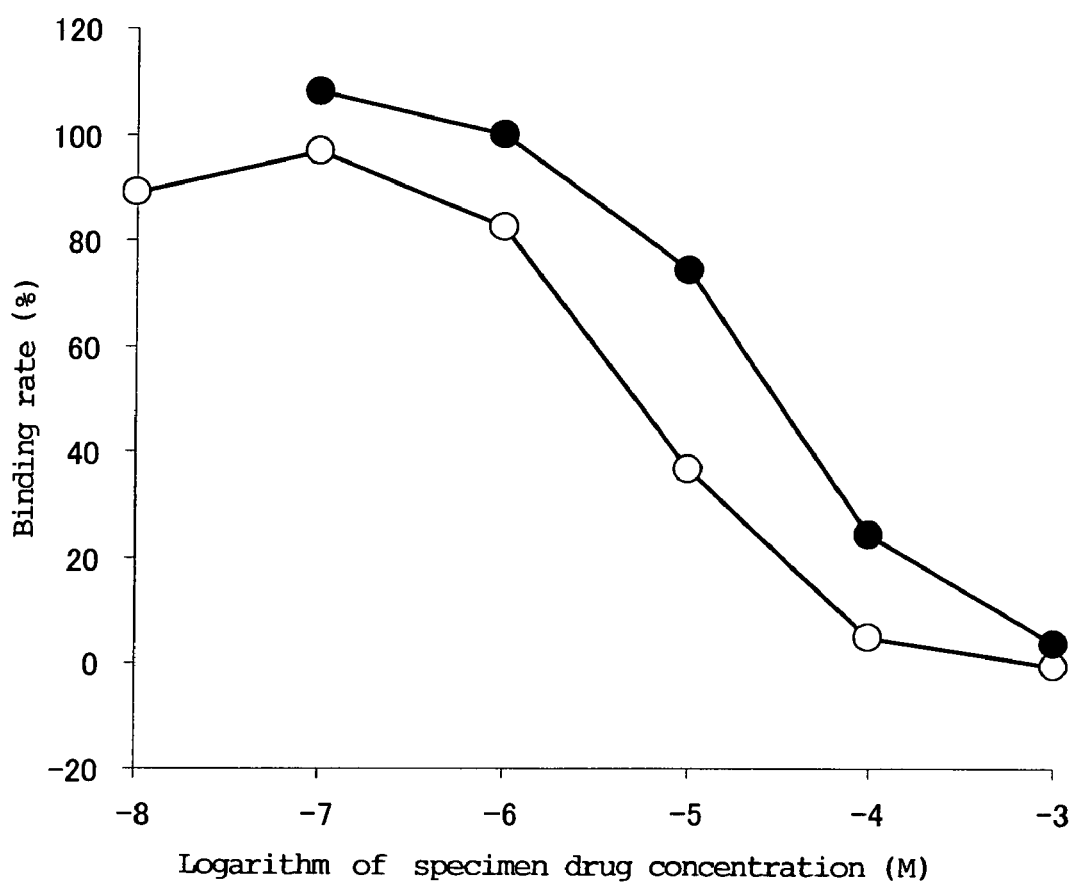
FIG. 2 indicates a change in binding affinity for a dopamine $D_2$ receptor, of a specimen drug. An abscissa axis indicates a concentration (molar concentration; logarithmic expression) of a specimen drug, and an ordinate axis indicates a ratio of binding of a dopamine $D_2$ receptor and [$^3$H]-spiperone. ●---● indicates a specimen compound obtained in Example 9, and ○---○ indicates TKS159 hydrochloride. As a concentration of a specimen drug grows higher, an amount of [$^3$H]-spiperone bound to a dopamine $D_2$ receptor is reduced. That is, it is indicated that a specimen drug binds to a dopamine D2 receptor by antagonizing [$^3$H]-spiperone binding thereto. It is seen that affinity of a specimen drug obtained in Example 9 for a dopamine $D_2$ receptor is weaker as compared with affinity of TKS159 hydrochloride.

The results are shown in FIG. 2. $IC_{50}$ is 34 µM, which is a higher concentration than 3.8 µM of TKS159 hydrochloride.

Example 3

Synthesis of N-acetyl-4-hydroxy-L-proline ethyl ester 345 g of acetic anhydride was added dropwise to a suspension of 600 g of 4-hydroxy-L-proline ethyl ester hydrochloride, 683 g of triethylamine and 2.4 L of chloroform at not higher than 10° C. while cooling. After stirring for 2 hours, water (0.6 L) was added, and the layers were separated. The organic layer was dried over magnesium sulfate, and concentrated under reduced pressure to obtain 1020 g of N-acetyl-4-hydroxy-L-proline ethyl ester as an oil.

IR (neat) ν $cm^{-1}$: 3402, 1740, 1626, 1456, 1278, 1195, 1085, 1035, 967, 864, 568

Example 4

Synthesis of N-acetyl-4-mesyloxy-L-proline ethyl ester 457 g of methanesulfonyl chloride was added dropwise to a solution of 1020 g of N-acetyl-4-hydroxy-L-proline ethyl ester, 435 g of triethylamine and 1.9 L of chloroform at not higher than 15° C. while cooling. After stirring for 30 minutes, 1N hydrochloric acid (0.6 L) was added, and the layers were separated. The organic layer was washed with 5% aqueous sodium bicarbonate (600 g), washed with water (0.6 L), dried over magnesium sulfate, and concentrated under reduced pressure to obtain 802 g of N-acetyl-4-mesyloxy-L-proline ethyl ester as an oil.

IR (neat) ν $cm^{-1}$: 3462, 1742, 1652, 1422, 1353, 1268, 1196, 1175, 958, 905, 531

Example 5

Synthesis of N-acetyl-4-azido-L-proline ethyl ester 243 g of sodium azide was added to a solution of 802 g of N-acetyl-4-mesyloxy-L-proline ethyl ester and 2.4 L of DMF, and the mixture was reacted at an inner temperature of 70° C. for 7 hours. The reaction solution was cooled, poured into ice water (4.8 L), and extracted with chloroform (3.2 L). The organic layer was dried over magnesium sulfate, and concentrated under reduced pressure to obtain 644 g of N-acetyl-4-azido-L-proline ethyl ester as an oil.

IR (neat) ν $cm^{-1}$: 3472, 2109, 1746, 1656, 1418, 1370, 1269, 1195, 1055, 1029, 615, 561

Example 6

Synthesis of (2S,4S)-N-acetyl-4-azido-2-hydroxymethyl-pyrrolidine 644 g of N-acetyl-4-azido-L-proline ethyl ester dissolved in 700 ml of ethanol was added dropwise to a suspension of 2.5 L of ethanol and 162 g of sodium borohydride at not higher than 10° C. while cooling. After overnight reaction, 35% hydrochloric acid (594 g) was added dropwise to the above mixture at not higher than 20° C. while cooling, and the solution was neutralized with sodium bicarbonate (24 g). After filtration, the solution was concentrated under reduced pressure while the solvent was substituted with 1.3 L of isopropyl alcohol, thereby to obtain 534 g of (2S,4S)-N-acetyl-4-azido-2-hydroxymethylpyrrolidine as an oil.

$^1$H—NMR (CDCL3) δ: 1.8 (1H, ddd), 2.1 (3H,s), 2.4 (1H,ddd), 2.9 (1H,d), 3.5 (1H,dd), 3.8 (2H,m), 4.2 (1H,ddd), 4.3 (1H, m), 4.7 (1H,OH) IR (neat) ν cm$^{-1}$: 3371, 2104, 1626, 1445, 1362, 1327, 1269, 1048, 907, 617, 560

Example 7

Synthesis of (2S, 4S)-N-acetyl-4-amino-2-hydroxymethyl-pyrrolidine 92.4 g of 10% Pd—C was added to a solution of 534 g of N-acetyl-4-azido-2-hydroxymethylpyrrolidine and 2.6 L of methanol, and this was hydrogenated (30 hours) at a normal pressure until the raw material disappeared, while the atmosphere in the container was substituted for hydrogen gas every one hour. After filtration, the solution was concentrated under reduced pressure to obtain 411 g of (2S, 4S)-N-acetyl-4-amino-2-hydroxymethylpyrrolidine, more specifically, (2S,4S)-(–)-1-acetyl-4-amino-2-hydroxymethyl-pyrrolidine as an oil.

$[α]_D^{20}$=–57.1° (c=1.28, MeOH) IR (neat) ν cm$^{-1}$: 3343, 1625, 1446, 1361, 1238, 1199, 1037, 957, 915, 757, 612

Example 8

Synthesis of 4-acetylamino-5-chloro-2-methoxy-N-[(2S,4S)-1-acetyl-2-hydroxymethyl-4-pyrrolidinyl]benzamide 9.84 g of 4-acetylamino-5-chloro-2-methoxybenzoic acid, and 4.5 g of triethylamine were dissolved in 40 ml of dichloromethane, and 4.60 g of ethyl chlorocarbonate was added dropwise to the solution at not higher than 10° C. After stirring at the same temperature for 30 minutes, a solution of 7.03 g of (2S,4S)-(–)-1-acetyl-4-amino-2-hydroxymethylpyrrolidine in dichloromethane (20 ml) was added dropwise. After stirring at the same temperature overnight, water (20 ml) was added, precipitated crystals were filtered, and the resulting crystals were dried in a warm air at 50 to 55° C. to obtain 11.74 g of 4-acetylamino-5-chloro-2-methoxy-N-[(2S,4S)-1-acetyl-2-hydroxymethyl-4-pyrrolidinyl]benzamide.

$^1$H—NMR (CDCL3) δ: 1.7 (1H, ddd), 2.1 (3H, s), 2.3 (3H, s), 2.5 (1H, ddd), 3.4 (1H, dd), 3.7 (1H, dd), 3.9 (1H, dd), 4.0 (3H, s), 4.1 (1H, dd), 4.3 (1H, m), 4.6 (2H, m), 7.8 (1H, s), 8.1 (1H, d), 8.2 (1H, s), 8.4 (1H, s). $^{13}$C—NMR (DMSO-d6), δ: 28.13, 28.97, 38.38, 52.04, 53.24, 59.66, 61.39, 63.20, 67.02, 124.58, 135.98, 143.55, 161.13, 161.18, 167.88, 141.17, 174.37. IR (KBr) ν cm$^{-1}$: 3251, 1697, 1629, 1563, 1511, 1457, 1397, 1309, 1238, 1194, 1080, 1049, 1013, 980, 638

Example 9

Synthesis of 4-amino-5-chloro-2-methoxy-N-[(2S,4S)-2-hydroxymethyl-4-pyrrolidinyl]benzamide monohydrochloride 11.74 g of 4-acetylamino-5-chloro-2-methoxy-N-[(2S,4S)-1-acetyl-2-hydroxymethyl-4-pyrrolidinyl]benzamide was dissolved in ethyl alcohol (60 ml), and sodium hydroxide (2.7 g) was added thereto. The mixture was heated at reflux for 8.5 hours. After addition of water (20 ml), the mixture was stirred at room temperature for 1 hour to filter insolubles off, and washed sufficiently with water (50 ml). The filtrate was concentrated under reduced pressure, n-butyl alcohol (50 ml) and a saturated brine solution (20 ml) were added to the resulting residue, and the layers were separated, followed by re-extraction with n-butyl alcohol (30 ml). The extract was concentrated under reduced pressure, methyl alcohol (50 ml) was added to the residue to dissolve it, and 18% (w/w) hydrochloric acid-containing methyl alcohol (6.5 g) was gradually added to adjust to a pH 6. After ice-cooling, precipitated crystals were filtered, and washed with a small amount of methyl alcohol. The resulting crystals were recrystallized from ethyl alcohol to obtain 5.5 g of the objective 4-amino-5-chloro-2-methoxy-N-[(2S,4S)-2-hydroxymethyl-4-pyrrolidinyl]benzamide monohydrochloride. mp 219-222° C., $[α]_D^{20}$: +4.20 (c=1.00, EtOH)

$^1$H—NMR(CD$_3$OD) δ: 1.98 (1H, ddd, J=13.6, 8.1, 5.5 Hz), 2.58 (1H, ddd, H=13.6, 8.3, 8.3 Hz), 3.38 (1H, dd, J=12.0, 4.0 Hz), 3.54 (1H, dd, J=12.0, 7.0 Hz), 3.79 (1H, dd, J=11.5, 5.1 Hz), 3.80 (1H, m), 3.92 (3H, s), 3.92 (1H, dd, J=11.5, 3.0 Hz), 4.68 (1H, m), 6.51 (1H, s), 7.82 (1H, s) $^{13}$C—NMR (CD$_3$OD) δ: 33.17, 50.31, 52.18, 56.67, 61.03, 62.33, 98.54, 110.86, 111.62, 133.29, 150.75, 159.83, 167.22. IR (KBr) ν cm$^{-1}$: 3418, 3385, 3325, 3212, 2437, 1637, 1588, 1455, 1207, 1161, 1048, 832.

Example 10

Using three beagle dogs as a test animal, 4-amino-5-chloro-2-methoxy-N-[(2S,4S)-2-hydroxymethyl-4-pyrrolidinyl]benzamide monohydrochloride obtained in Example 9 was repeatedly administered orally at a dose of 100 mg/kg once a day for 4 weeks. Thereafter, the animals were sacrificed by exsanguination from carotid artery under anesthesia, and the brain, aorta, heart, lung, and liver were extracted. These organs were examined with naked eyes, fixed with a 0.1% phosphate-buffered 10% formalin solution, and stored. Each organ was embedded in paraffin, and sliced to prepare a hematoxine orange-stained sample. Pathohistological test on the sections was performed using a light microscope. Abnormality was not seen in any organ with naked eyes. In addition, abnormality was not seen also in a pathohistological test, and encephalomalacia, arteritis and thrombus formation were not recognized.

Example 11

Five Sprague-Dawley male rats, 4 week age, weighing each 160.3 to 169.5 g, were reared for 8 days for quarantine and training were handled as one group, and they were grouped into four groups of a control group, a 300 mg/kg administration, a 1000 mg/kg administration, and a 2000 mg/kg administration. 4-Amino-5-chloro-2-methoxy-N-[(2S,4S)-2-hydroxymethyl-4-pyrrolidinyl] benzamide monohydrochloride obtained in Example 9 was ground with a mortar, the powder was added so that the compound was contained at 300 mg, 1000 mg or 2000 mg in 10 ml of a 0.5% aqueous methylcellulose solution (manufactured by Wako Pure Chemical Industries, Ltd.; prepared using Japanese Pharmacopoeia injectable water), and the solution was stirred to prepare an administration specimen. Administration specimens for 7 days were prepared at one time, once per week, stored in a refrigerator, and used. One-time dose was defined to be 10 ml/kg, and the specimen was forcibly administered orally at 9 o'clock to 12 o'clock for 28 days once a day using a rat stomach tube. Only a 0.5% aqueous methylcellulose solution was administered at 10 ml/kg to a control group.

During training and drug administration period, a solid feed (CE-2 manufactured by CLEA Japan Inc.) and tap water were freely given.

After termination of the administration period, all cases were subjected to necropsy, an organ and a tissue such as brain, heart, aorta, lung, pancreas, liver, and cava were observed with naked eyes and histologically, and subjected to a pathohistological test. Abnormality was not seen with naked eyes in any organ. In addition, also in a pathohistological test, abnormality was not seen, and encephalomalacia, arteritis and thrombus formation were not recognized.

Example 12

Measurement of relaxation reaction of 4-amino-5-chloro-2-methoxy-N-[(2S,4S)-2-hydroxymethyl-4-pyrrolidinyl]benzamide monohydrochloride in rat-extracted sample Regarding the drug obtained in Example 9, a degree of action of promoting the movement of the digestive tract was measured using an esophagus sample extracted from a rat.

Figure 3:
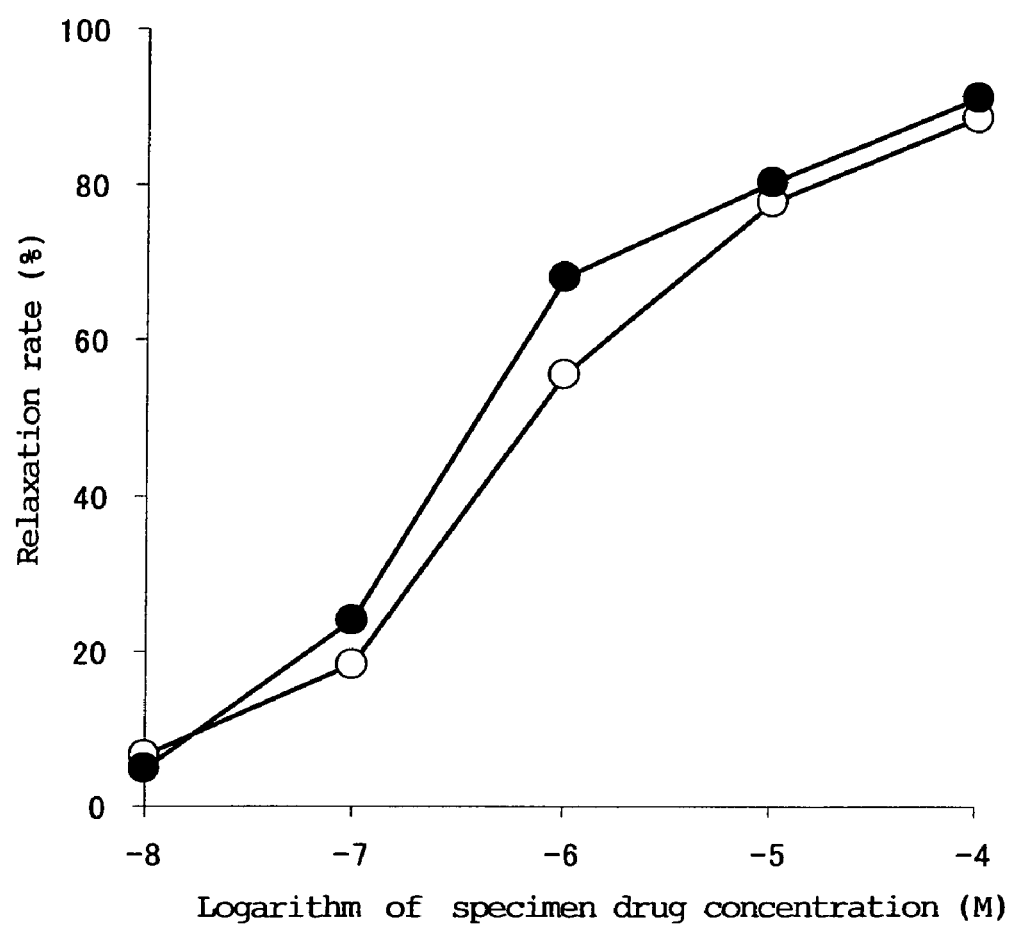
FIG. 3 indicates a degree of a relaxing reaction of a specimen drug in a rat-extracted specimen. An abscissa axis indicates a concentration (molar concentration; logarithm expression) of a specimen drug, and an ordinate axis indicates a ratio of relaxation in a rat-extracted specimen. ●---● indicates a specimen compound obtained in Example 9, and ○---○ indicates TKS159-hydrochloride. As a concentration of a specimen drug grows higher, relaxation of a specimen is caused in a concentration-dependent manner, and it is seen that action of a drug obtained in Example 9 is stronger as compared with TKS159 hydrochloride.

An esophagus in a chest cavity was extracted from a Wistar male rat, and muscularis propria sample containing longitudinal muscle and circular muscle was removed to prepare a muscularis mucosae sample having a length of about 2 cm. The sample was immersed in a nutrient solution (containing NaCl 118.5, KCl 4.7, $CaCl_2$ 1.3, $MgSO_4$ 0.6, $NaHCO_3$ 25.0, $KH_2PO_4$ 1.2, and glucose 11.1 (unit mM)), and constriction of the sample and stability of the constriction were confirmed at 32°C using $3 \times 10^{-6}$ M carbachol while a 95% $O_2$/5% $CO_2$ mixed gas was flown, each 1 µM of methysergide, ketanserin and granisetron were added, the drug obtained in Example 9 was accumulatively applied at a common ratio of 3 after 30 minutes, and a degree of relaxation was isotonically (stationary tension; about 0.5 g) measured via a transducer. Separately, the same procedure was also performed regarding TKS159 hydrochloride, and an intensity of the action was compared. The results are shown in FIG. 3. $EC_{50}$ was 0.7 µM, which is a lower concentration than 1.1 µM of TKS159 hydrochloride.

Example 13

Using a ddy male mouse, the drug obtained in Example 9 and TKS159 were suspended in 0.5% methylcellulose for oral administration, and were dissolved in a physiological saline for intravenous administration. This was administered by a forced oral administration method and an intravenous administration method using a probe, and acute toxicity was observed.

| Administration method | Administration material | Dose mg/kg | Survival |
|---|---|---|---|
| Oral administration | Example 9 drug | 1080 | 5 survivals among 5 |
| | | 1320 | 3 survivals among 5 |
| | TKS159 hydrochloride | 720 | 3 survivals among 4 |
| | | 880 | 1 survival among 5 |
| | | 1080 | No survival among 2 |
| Intravenous administration | Example 9 drug | 32 | 6 survivals among 6 |
| | | 48 | 1 survival among 5 |
| | | 59 | 1 survival among 6 |
| | | 72 | 1 survival among 6 |
| | TKS159 hydrochloride | 72 | 5 survivals among 6 |
| | | 88 | 4 survivals among 6 |
| | | 108 | 4 survivals among 6 |
| | | 132 | No survival among 6 |

Example 14

50 g of the drug obtained in Example 9, 650 g of lactose, and 200 g of crystalline cellulose were weighed, this was placed into a fluidized layer granulator, and sprayed with a 5% aqueous solution of 30 g of a binder hydroxypropylcellulose to obtain granulated powders. Then, 50 g of a disintegrating agent calcium carboxymethylcellulose and 20 g of a lubricant magnesium stearate were added to granulated powders, and these were mixed. The resulting granulated powders for compression were molded under pressure to obtain tablets, one tablet weighing 100 mg.

Separately, using tablets obtained herein, a film coating solution prepared using 48 g of hydroxypropylmethylcellulose, 7.2 g of polyethylene glycol 6000, 1.8 g of talc, 3 g of titanium oxide and 550 cc of purified water was coated to a weight of one tablet of 105 mg, to obtain a film-coated tablet.

Reference Example

TKS159 was repeatedly administered orally to each group of two male beagle dogs for 4 weeks at a dose of 10, 30 and 100 mg/kg, these were observed and, as a result, thrombus formation was recognized in a lung artery and a heart coronary artery, and slight bleeding was recognized in a cavity surrounding a blood vessel in a cerebral parenchyma in a death case of a 100 mg/kg administration group. In a survival case of a 100 mg/kg administration group, big thrombus formation was recognized in a left ventricle, and thrombus formation was recognized in a kidney arcuate artery and an interlobar artery. Separately, beagle dogs (female and male) were divided into 4 groups consisting of 6, 4, 4 and 6 dogs and, among them, to 3 groups were repeatedly administered orally TKS 159 at a dose of 2.5, 6.0 and 15.0 mg/kg, and to a control group was repeatedly administered orally an excipient, for 13 weeks, and observation of the general status and various tests were performed. Further, regarding a control group and a case of a part of a 15.0 mg/kg administration group, after a repeated administration period for 13 weeks, a recovery test of no administration of a drug was performed for 4 weeks, and then the same test was performed. As a result of the test, in two cases of the 15.0 mg/kg administration group, arteritis was recognized, and a site thereof was around a spinal nerve root, and costa artery, cerebral pia mater, thymus and bladder. In other one case, necrosis of an artery septum and surrounding cell infiltration were recognized in cerebellumpiamater, lung, coronary artery, liver, bladder, stomach, vagina, intestine and diaphragm. Separately, beagle dogs (female and male) were divided into 4 groups containing 5, 3, 3 and 5 dogs and, among them, to 3 groups was repeatedly administered orally TKS159 at a dose of 0.25, 0.75 and 2.25 mg/kg, to a control group was repeatedly administered an excipient orally, for 52 weeks, and observation of the general status and various tests were performed. Further, regarding a control group and a case of a part of a 2.25 mg/kg administration group, after a repeated administration period for 52 weeks, a recovery test of no administration of a drug was performed for 4 weeks, and then the same test was performed. As a result of a test, in a 52 week repeated administration toxicity test, arteritis was observed in thighbone marrow and mediastinal lymph node in one case among male 5 cases of the 2.25 mg/kg administration group, and malacia was seen in piriform lobe and hippocampus in other one case.

INDUSTRIAL APPLICABILITY

In the present invention, an ameliorant for improving the movement of the digestive tract comprising, as an active ingredient, 4-amino-5-chloro-2-methoxy-N-[(2S,4S)-2-hydroxymethyl-4-pyrrolidinyl]benzamide or an acid addition salt thereof which has high binding affinity for a serotonin receptor 4 (5HT$_4$) and capable of avoiding side effect occurrence such as thrombus formation and arteritis concomitantly caused inevitably in administration of 4-amino-5-chloro-2-methoxy-N-[(2S,4S)-1-ethyl-2-hydroxymethyl-4-pyrrolidinyl]benzamide or an acid addition salt thereof, or a medicinal composition containing the ameliorant as an active ingredient and a pharmaceutically acceptable carrier can be provided. Since it is an indispensable attribute for a medicinal compound that side effect is avoided as much as possible, the ameliorant of the present invention is effective and safe with no side effect occurrence, and thus it is useful as a medicine.

The invention claimed is:

1. A treating method for promoting the movement of the digestive tract, which consists of administering isolated and optically active 4-amino-5-chloro-2-methoxy-N-[(2S,4S)-2-hydroxymethyl-4-pyrrolidinyl]benzamide or an acid addition salt thereof which has high binding affinity for a serotonin receptor 4 (5HT$_4$) and does not cause arteritis or thrombus formation, and optionally a pharmaceutically acceptable carrier.

2. A method for improving the movement of the digestive tract of a human or an animal while avoiding occurrence of arteritis, thrombus formation or encephalomalacia, which consists of administering isolated and optically active 4-amino-5-chloro-2-methoxy-N-[(2S,4S)-2-hydroxymethyl-4-pyrrolidinyl]benzamide or an acid addition salt thereof and optionally a pharmaceutically acceptable carrier to a human or a mammal.

* * * * *